United States Patent
Zhu et al.

(10) Patent No.: US 7,970,471 B2
(45) Date of Patent: *Jun. 28, 2011

(54) CAPTURE VERIFICATION FOR CARDIAC RESYNCHRONIZATION PACING OPTIMIZATION

(75) Inventors: Qingsheng Zhu, Little Canada, MN (US); Julio C. Spinelli, Shoreview, MN (US); Jiang Ding, Maplewood, MN (US); Yinghong Yu, Maplewood, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 1000 days.

This patent is subject to a terminal disclaimer.

(21) Appl. No.: 11/776,699

(22) Filed: Jul. 12, 2007

(65) Prior Publication Data

US 2008/0015650 A1    Jan. 17, 2008

Related U.S. Application Data

(63) Continuation of application No. 11/168,099, filed on Jun. 28, 2005, now Pat. No. 7,245,970, which is a continuation of application No. 09/999,255, filed on Oct. 31, 2001, now Pat. No. 6,937,901.

(51) Int. Cl.
*A61N 1/18* (2006.01)
(52) U.S. Cl. .................................................. 607/27
(58) Field of Classification Search ............. 607/4–5, 607/9, 27–28; 600/510
See application file for complete search history.

(56) References Cited

U.S. PATENT DOCUMENTS

| | | | |
|---|---|---|---|
| 4,114,627 A | 9/1978 | Lewyn et al. | |
| 5,003,975 A | 4/1991 | Hafelfinger et al. | |
| 5,222,493 A | 6/1993 | Sholder | |
| 5,324,310 A | 6/1994 | Greeninger et al. | |
| 5,331,966 A | 7/1994 | Bennett et al. | |
| 5,431,693 A | 7/1995 | Schroeppel | |
| 5,443,485 A | 8/1995 | Housworth et al. | |
| 5,571,144 A | 11/1996 | Schroeppel | |
| 5,601,615 A | 2/1997 | Markowitz et al. | |
| 5,718,720 A | 2/1998 | Prutchi et al. | |
| 5,766,225 A | 6/1998 | Kramm | |
| 5,843,136 A | 12/1998 | Zhu et al. | |
| 5,861,012 A | 1/1999 | Stroebel | |
| 5,873,898 A | 2/1999 | Hemming et al. | |
| 6,128,535 A | 10/2000 | Maarse | |
| 6,782,291 B1 | 8/2004 | Bornzin et al. | |
| 6,937,901 B2 * | 8/2005 | Zhu et al. ............... | 607/27 |
| 7,215,992 B2 | 5/2007 | Stahmann et al. | |
| 7,245,970 B2 * | 7/2007 | Zhu et al. ............... | 607/28 |
| 2004/0133247 A1 | 7/2004 | Stahmann et al. | |

* cited by examiner

*Primary Examiner* — Mark W Bockelman
(74) *Attorney, Agent, or Firm* — Schwegman, Lundberg & Woessner, P.A.

(57) ABSTRACT

A system and method for automatically selecting among a plurality of pacing modes based upon capture detection. Patients suffering from heart failure may be optimally treated with different resynchronization pacing modes or configurations. By detecting whether capture is being achieved by a particular configuration or mode, a device is able to automatically switch to one that is both optimal in treating the patient and is successful in capturing the heart with pacing pulses.

20 Claims, 3 Drawing Sheets

CAPTURE VERIFICATION FOR CARDIAC RESYNCHRONIZATION PACING OPTIMIZATION

CROSS-REFERENCE TO RELATED APPLICATION

This application is a continuation of U.S. patent application Ser. No. 11/168,099, filed on Jun. 28, 2005, now issued as U.S. Pat. No. 7,245,970,which is a continuation of U.S. patent application Ser. No. 09/999,255, filed on Oct. 31, 2001, now issued as U.S. Pat. No. 6,937,901, the specifications of which are incorporated herein by reference.

FIELD OF THE INVENTION

This patent application pertains to methods and apparatus for cardiac rhythm management. In particular, it relates to methods and apparatus for providing cardiac resynchronization therapy.

BACKGROUND

Cardiac rhythm management devices are implantable devices that provide electrical stimulation to selected chambers of the heart in order to treat disorders of cardiac rhythm. A pacemaker, for example, is a cardiac rhythm management device that paces the heart with timed pacing pulses. The most common condition for which pacemakers are used is in the treatment of bradycardia, where the ventricular rate is too slow. Atrio-ventricular conduction defects (i.e., AV block) that are permanent or intermittent and sick sinus syndrome represent the most common causes of bradycardia for which permanent pacing may be indicated. If functioning properly, the pacemaker makes up for the heart's inability to pace itself at an appropriate rhythm in order to meet metabolic demand by enforcing a minimum heart rate.

Pacing therapy can also be used in the treatment of congestive heart failure (CHF), which is a clinical syndrome in which an abnormality of cardiac function causes cardiac output to fall below a level adequate to meet metabolic demand. CHF can be due to a variety of etiologies with that due to ischemic heart disease being the most common. Some CHF patients suffer from some degree of AV block or are chronotropically deficient such that their cardiac output can be improved with conventional bradycardia pacing. It has also been shown, however, that some CHF patients suffer from intraventricular and/or interventricular conduction defects (e.g., bundle branch blocks) such that their cardiac outputs can be increased by improving the synchronization of ventricular contractions with electrical stimulation. Other conduction defects can occur in the atria. Cardiac rhythm management devices have therefore been developed which provide electrical stimulation to the atria and/or ventricles in an attempt to improve the coordination of cardiac contractions, termed cardiac resynchronization therapy.

SUMMARY OF THE INVENTION

The present invention is a method and system for automatically optimizing the operation of a cardiac rhythm management device based upon verification of capture during device operation. In accordance with the invention, pacing pulses are output through selected pacing channels making up a selected pacing configuration in accordance with a programmed pacing mode associated with the selected pacing configuration. A capture verification test is performed at a selected time to test a selected sensing/pacing channel for presence or loss of capture during a pacing pulse, the capture verification test being performed by sensing whether an evoked response occurs during a capture detection window following the output of a pacing pulse. Upon detection of a loss of capture in a pacing channel making up the selected pacing configuration, the device switches from the selected pacing configuration and associated pacing mode to a next pacing configuration and associated pacing mode contained in an ordered list. The pacing configurations and associated modes in the ordered list may be ranked in order of therapeutic benefit as determined by clinical testing of a particular patient. In one embodiment, upon detection of a loss of capture in a pacing channel, a next pacing configuration and associated pacing mode that does not employ the pacing channel in which a loss of capture was detected is selected from the ordered list. The list of pacing configurations and associated pacing modes may include, for example, a biventricular pacing configuration, a left ventricular-only pacing configuration, a right ventricular-only pacing configuration, and a configuration in which no pacing is performed. The pacing mode associated with each pacing configuration may include various pacing parameters such as an AV delay interval employed in atrial tracking and/or sequential atrio-ventricular pacing modes.

DETAILED DESCRIPTION

Cardiac rhythm management devices for delivering resynchronization therapy may be configured in a number of different ways and with a number of different parameter settings. The effectiveness of a particular configuration and parameter set, however, depends upon the extent to which the resynchronization pacing pulses are achieving capture of the heart. As described below, a device may be configured to test whether capture is being achieved and modify its operation accordingly.

1. Hardware Platform

Pacemakers are typically implanted subcutaneously or submuscularly in a patient's chest and have leads threaded intravenously into the heart to connect the device to electrodes used for sensing and pacing. Leads may also be positioned on the epicardium by various means. A programmable electronic controller causes the pacing pulses to be output in response to lapsed time intervals and sensed electrical activity (i.e., intrinsic heart beats not as a result of a pacing pulse). Pacemakers sense intrinsic cardiac electrical activity by means of internal electrodes disposed near the chamber to be sensed. A depolarization wave associated with an intrinsic contraction of the atria or ventricles that is detected by the pacemaker is referred to as an atrial sense or ventricular sense, respectively. In order to cause such a contraction in the absence of an intrinsic beat, a pacing pulse (either an atrial pace or a ventricular pace) with energy above a certain pacing threshold is delivered to the chamber.

Figure 1:
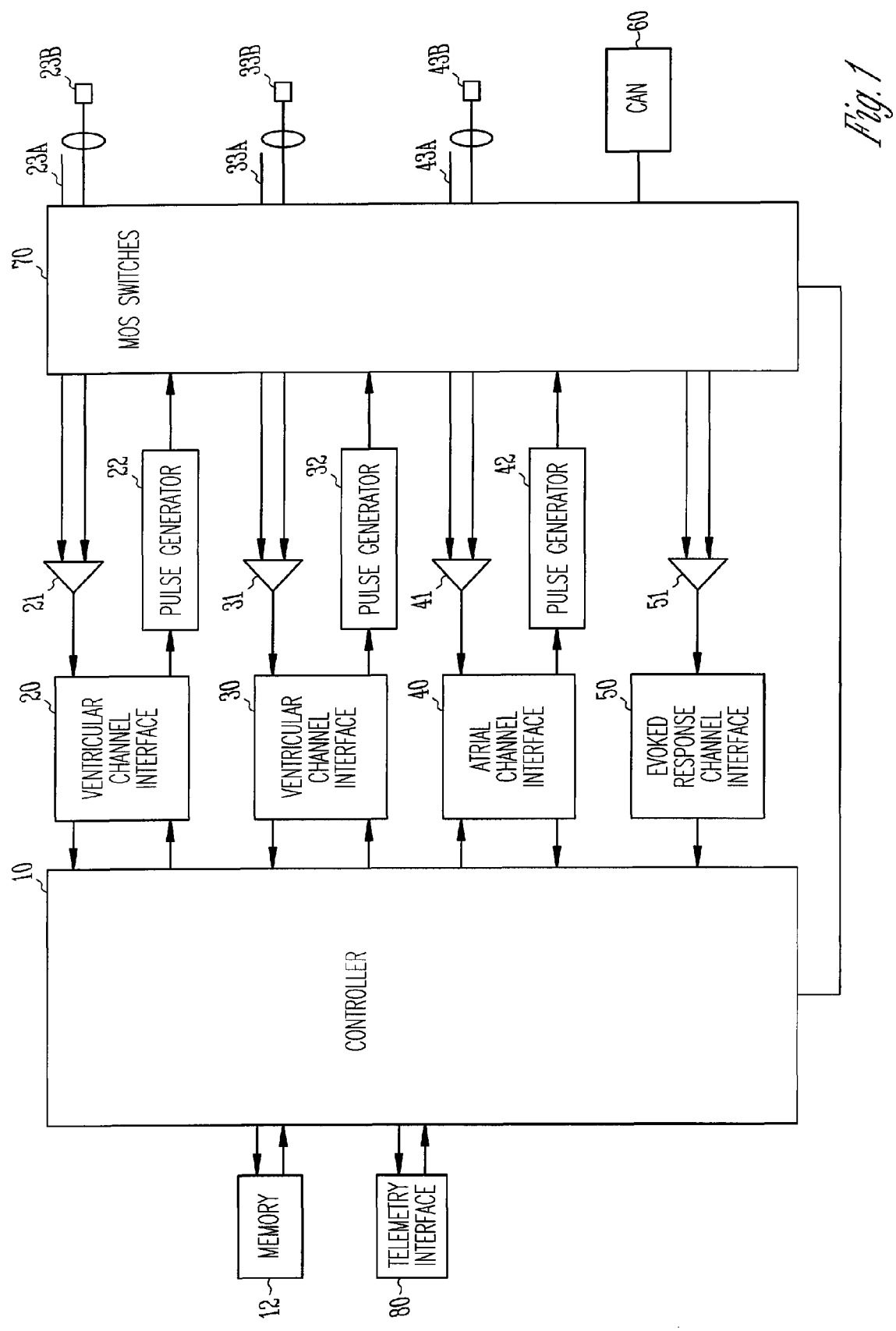
FIG. 1 is a system diagram of a pacemaker configured for biventricular pacing and sensing.

A block diagram of a multi-site pacemaker having three sensing/pacing channels is shown in FIG. 1. (As the term is used herein, a "pacemaker" should be taken to mean any cardiac rhythm management device, such as an implantable cardioverter/defibrillator, with a pacing functionality.) The controller of the pacemaker is made up of a microprocessor 10 communicating with a memory 12 via a bidirectional data bus, where the memory 12 comprises a ROM (read-only memory) for program storage and a RAM (random-access memory) for data storage. The controller can be implemented by other types of logic circuitry (e.g., discrete components or programmable logic arrays) using a state machine type of design, but a microprocessor-based system is preferable. The controller is capable of operating the pacemaker in a number of programmed modes where a programmed mode defines how pacing pulses are output in response to sensed events and expiration of time intervals. A telemetry interface 80 is also provided for communicating with an external programmer.

The multiple sensing/pacing channels may be configured to deliver biventricular pacing, biatrial pacing, or multi-site pacing of a single chamber. Illustrated in FIG. 1 is a configuration with one atrial and two ventricular sensing/pacing channels for delivering biventricular pacing. The atrial sensing/pacing channel in FIG. 1 comprises ring electrode 43a, tip electrode 43b, sense amplifier 41, pulse generator 42, and an atrial channel interface 40 which communicates bidirectionally with a port of microprocessor 10. The device also has two ventricular sensing/pacing channels that similarly include ring electrodes 23a and 33b, tip electrodes 23b and 33b, sense amplifiers 21 and 31, pulse generators 22 and 32, and ventricular channel interfaces 20 and 30. Incorporated into each sensing/pacing channel is thus a pacing channel made up of the pulse generator connected to the electrode and a sensing channel made up of the sense amplifier connected to the electrode. The electrodes are electrically connected to the device by means of a lead. For each channel, the same lead and electrode are used for both sensing and pacing. The pacemaker also has an evoked response sensing channel that comprises an evoked response channel interface 50 and a sense amplifier 51. The channel interfaces include analog-to-digital converters for digitizing sensing signal inputs from the sensing amplifiers, registers that can be written to for adjusting the gain and threshold values of the sensing amplifiers, and, in the case of the ventricular and atrial channel interfaces, registers for controlling the output of pacing pulses and/or changing the pacing pulse amplitude.

The controller 10 controls the overall operation of the device in accordance with programmed instructions stored in memory, including controlling the delivery of paces via the pacing channels, interpreting sense signals received from the sensing channels, and implementing timers for defining escape intervals and sensory refractory periods. The sensing circuitry of the pacemaker detects a chamber sense, either an atrial sense or ventricular sense, when a sense signal (i.e., a voltage sensed by an electrode representing cardiac electrical activity, sometimes called an electrogram signal) generated by a particular channel exceeds a specified intrinsic detection threshold. Pacing algorithms used in particular pacing modes employ such senses to trigger or inhibit pacing. Both the pacing mode and the pacing configuration, which specifies which of the available pacing channels in a device are to be used to deliver paces, are implemented by appropriate programming of the controller.

2. Bradycardia Pacing Modes

Bradycardia pacing modes refer to pacing algorithms used to pace the atria and/or ventricles when the intrinsic atrial and/or ventricular rate is inadequate due to, for example, AV conduction blocks or sinus node dysfunction. Such modes may either be single-chamber pacing, where either an atrium or a ventricle is paced, or dual-chamber pacing in which both an atrium and a ventricle are paced. The modes are generally designated by a letter code of three positions where each letter in the code refers to a specific function of the pacemaker. The first letter refers to which heart chambers are paced and which may be an A (for atrium), a V (for ventricle), D (for both chambers), or O (for none). The second letter refers to which chambers are sensed by the pacemaker's sensing channels and uses the same letter designations as used for pacing. The third letter refers to the pacemaker's response to a sensed P wave from the atrium or an R wave from the ventricle and may be an I (for inhibited), T (for triggered), D (for dual in which both triggering and inhibition are used), and O (for no response). Modem pacemakers are typically programmable so that they can operate in any mode which the physical configuration of the device will allow. Additional sensing of physiological data allows some pacemakers to change the rate at which they pace the heart in accordance with some parameter correlated to metabolic demand. Such pacemakers are called rate-adaptive pacemakers and are designated by a fourth letter added to the three-letter code, R.

Pacemakers can enforce a minimum heart rate either asynchronously or synchronously. In asynchronous pacing, the heart is paced at a fixed rate irrespective of intrinsic cardiac activity. There is thus a risk with asynchronous pacing that a pacing pulse will be delivered coincident with an intrinsic beat and during the heart's vulnerable period which may cause fibrillation. Most pacemakers for treating bradycardia today are therefore programmed to operate synchronously in a so-called demand mode where sensed cardiac events occurring within a defined interval either trigger or inhibit a pacing pulse. Inhibited demand pacing modes utilize escape intervals to control pacing in accordance with sensed intrinsic activity. In an inhibited demand mode, a pacing pulse is delivered to a heart chamber during a cardiac cycle only after expiration of a defined escape interval during which no intrinsic beat by the chamber is detected. If an intrinsic beat occurs during this interval, the heart is thus allowed to "escape" from pacing by the pacemaker. Such an escape interval can be defined for each paced chamber. For example, a ventricular escape interval can be defined between ventricular events so as to be restarted with each ventricular sense or pace. The inverse of this escape interval is the minimum rate at which the pacemaker will allow the ventricles to beat, sometimes referred to as the lower rate limit (LRL).

In atrial tracking pacemakers (i.e., VDD or DDD mode), another ventricular escape interval is defined between atrial and ventricular events, referred to as the atrio-ventricular interval (AVI). The atrio-ventricular interval is triggered by an atrial sense or pace and stopped by a ventricular sense or pace. A ventricular pace is delivered upon expiration of the atrio-ventricular interval if no ventricular sense occurs before. Atrial-tracking ventricular pacing attempts to maintain the atrio-ventricular synchrony occurring with physiological beats whereby atrial contractions augment diastolic filling of the ventricles. If a patient has a physiologically normal atrial rhythm, atrial-tracking pacing also allows the ventricular pacing rate to be responsive to the metabolic needs of the body.

A pacemaker can also be configured to pace the atria on an inhibited demand basis. An atrial escape interval is then defined as the maximum time interval in which an atrial sense must be detected after a ventricular sense or pace before an atrial pace will be delivered. When atrial inhibited demand pacing is combined with atrial-triggered ventricular demand pacing (i.e., DDD mode), the lower rate limit interval is then the sum of the atrial escape interval and the atrio-ventricular interval.

Another type of synchronous pacing is atrial-triggered or ventricular-triggered pacing. In this mode, an atrium or ventricle is paced immediately after an intrinsic beat is detected in the respective chamber. Triggered pacing of a heart chamber is normally combined with inhibited demand pacing so that a pace is also delivered upon expiration of an escape interval in which no intrinsic beat occurs. Such triggered pacing may be employed as a safer alternative to asynchronous pacing when, due to far-field sensing of electromagnetic interference from external sources or skeletal muscle, false inhibition of pacing pulses is a problem. If a sense in the chamber's sensing channel is an actual depolarization and not a far-field sense, the triggered pace is delivered during the chamber's physiological refractory period and is of no consequence.

3. Cardiac Resynchronization Therapy

Cardiac resynchronization therapy is pacing stimulation applied to one or more heart chambers in a manner that restores or maintains synchronized contractions of the atria and/or ventricles and thereby improves pumping efficiency. Certain patients with conduction abnormalities may experience improved cardiac synchronization with conventional single-chamber or dual-chamber pacing as described above. For example, a patient with left bundle branch block may have a more coordinated contraction of the ventricles with a pace than as a result of an intrinsic contraction. Resynchronization pacing, however, may also involve delivering paces to multiple sites of a heart chamber or pacing both ventricles and/or both atria in accordance with a resynchronization pacing mode as described below. Ventricular resynchronization pacing is useful in treating heart failure because, although not directly ionotropic, resynchronization results in a more coordinated contraction of the ventricles with improved pumping efficiency and increased cardiac output. Resynchronization pacing of the atria may also be beneficial in certain heart failure patients, particularly for preventing the onset of atrial arrhythmias.

One way to deliver resynchronization therapy is to pace a site with a synchronous bradycardia pacing mode and then deliver one or more resynchronization paces to one or more additional pacing sites in a defined time relation to one or more selected sensing and pacing events that either reset escape intervals or trigger paces in the bradycardia pacing mode. One such resynchronization pacing mode may be termed offset resynchronization pacing. In this mode, a first site is paced with a bradycardia mode, and a second site receives a resynchronization pace at an offset interval with respect to the pace delivered to the first site. The offset interval may be zero in order to pace both sites simultaneously, positive in order to pace the first site after the second, or negative to pace the first site before the second. For example, in biventricular resynchronization pacing, one ventricle is paced with a bradycardia mode while the contralateral ventricle receives resynchronization paces at the specified biventricular offset interval. The offset interval would normally be individually specified to optimize cardiac output in a particular patient. Ventricular resynchronization can also be achieved in certain patients by pacing at a single unconventional site, such as the left ventricle instead of the right ventricle. In such a mode, right ventricular senses may be used to trigger left ventricular paces or used to define an escape interval that upon expiration causes delivery of a left ventricular pace.

4. Capture Verification

In order for a pacemaker to control the heart rate and/or enhance pumping efficiency in the manner described above, the paces delivered by the device must achieve "capture," which refers to causing sufficient depolarization of the myocardium that a propagating wave of excitation and contraction result (i.e., a heart beat). A pacing pulse that does not capture the heart is thus an ineffective pulse. This not only wastes energy from the limited energy resources (battery) of pacemaker, but can have deleterious physiological effects as well, since a pacemaker that is not achieving capture is not performing its function in enforcing a minimum heart rate in the case of bradycardia pacing, or in synchronizing cardiac contractions in the case of resynchronization therapy. A number of factors can determine whether a given pacing pulse will achieve capture including the energy of the pulse, which is a function of the pulse's amplitude and duration or width, and the integrity and physical disposition of the pacing lead.

A common technique used to determine if capture is present during a given cardiac cycle is to look for an "evoked response" immediately following a pacing pulse. The evoked response is the wave of depolarization that results from the pacing pulse and evidences that the paced chamber has responded appropriately and contracted. By detecting the evoked P-wave or evoked R-wave, the pacemaker is able to detect whether the pacing pulse (A-pulse or V-pulse) was effective in capturing the heart, that is, causing a contraction in the respective heart chamber. In order for a pacemaker to detect whether an evoked P-wave or an evoked R-wave occurs immediately following an A-pulse or a V-pulse, a period of time, referred to as the atrial capture detection window or the ventricular capture detection window, respectively, starts after the generation of the pulse. Sensing channels are normally rendered refractory (i.e., insensitive) for a specified time period immediately following a pace in order to prevent the pacemaker from mistaking a pacing pulse or afterpotential for an intrinsic beat. This is done by the pacemaker controller ignoring sensed events during the refractory intervals, which are defined for both atrial and ventricular sensing channels and with respect to both atrial and ventricular pacing events. Furthermore, a separate period that overlaps the early part of a refractory interval is also defined, called a blanking interval during which the sense amplifiers are blocked from receiving input in order to prevent their saturation during a pacing pulse. If the same sensing channels are used for both sensing intrinsic activity and evoked responses, the capture detection window must therefore be defined as a period that supercedes the normal refractory period so that the sensing circuitry within the pacemaker becomes sensitive to an evoked P-wave or R-wave.

Capture verification can be performed by delivering a pacing pulse and attempting to sense an evoked response during the capture detection window through an evoked response sensing channel which may be either a channel normally used for sensing intrinsic activity or a dedicated channel. In an exemplary embodiment, a capture verification test is performed by a multi-site pacemaker such as shown in FIG. 1 using a dedicated evoked response sensing channel. In this test, it is determined whether or not a sensing/pacing channel is achieving capture with the pacing pulses delivered by the channel's electrode. The evoked response sensing channel includes a sense amplifier for sensing an evoked response generated after a pacing pulse is delivered. The evoked response sensing channel is connected to a selected electrode of the pacemaker's sensing/pacing channels by means of a switching circuit. After switching the input of the evoked response sensing channel to the electrode that is to be tested to verify capture and the delivery of a pacing pulse, an evoked response is either detected or not by comparing the output of the sensing amplifier to a specified evoked response detection threshold, thus signifying the presence or loss of capture, respectively. Although the same electrode can be used for pacing and evoked response detection during a capture verification test, the input of the evoked response sensing channel preferably is switched to an electrode of another sensing/pacing channel. The particular electrode used for evoked response detection can be selected in accordance with which electrode is placed in a location where an evoked response due to the pacing electrode can be most easily sensed. The sense amplifier of the evoked response sensing channel is then blanked during the capture verification test for a specified blanking period following a pacing pulse output by the tested sensing/pacing channel. The blanking period is followed by a capture detection window during which an evoked response may be sensed by the evoked response sensing channel. In an exemplary embodiment, the blanking period may be approximately 10 ms, and the width of the capture detection window may range from 50 to 350 ms.

Figure 2:
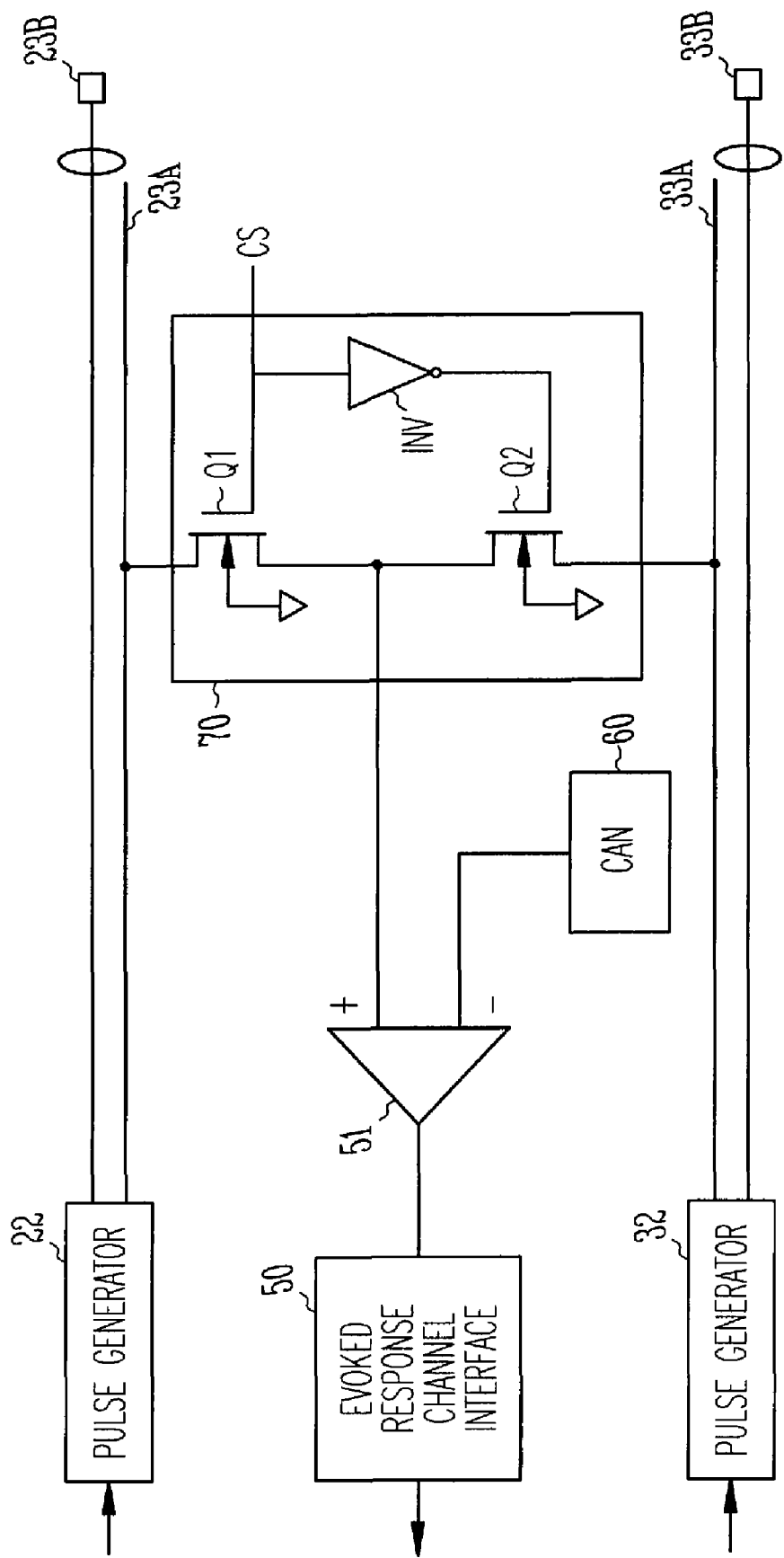
FIG. 2 illustrates an exemplary switching circuit.

Referring back to FIG. 1, the electrodes are connected to the sense amplifiers by means of a switching circuit 70 which enables the amplifiers to be connected to selected tip or ring electrodes of any of the sensing/pacing channels that connect through the switching circuit 70. Each sense amplifier amplifies the voltage difference between two inputs, and the inputs may be selected from any of the tip or ring electrodes or the pacemaker case or can 60, which is also electrically connected to the switching circuit. The configuration of the switching circuit 70 is preferably implemented as an array of MOSFET transistors controlled by outputs of the controller 10. FIG. 2 shows a portion of a basic exemplary switching circuit. In this circuit, a pair of MOSFET transistors Q1 and Q2 along with inverter INV form a double-pole switch that switches one of the inputs to amplifier 51 between ring electrode 23a and 33a. The other input is shown as being connected to can 60, but in other embodiments it may also be switched to one of the electrodes by means of the switching circuit. In a more complicated version of the same basic pattern, the switching circuit 70 may be able to switch the inputs of the evoked response sensing channel to any of the tip or ring electrodes of the sensing/pacing channels or to the can 60.

5. Automatic Selection of Pacing Configuration

Cardiac rhythm management devices for resynchronization pacing can operate in a number of pacing configurations that specify the location and number of pacing sites. Each such pacing configuration employs a particular pacing mode that specifies how pacing pulses are to be output in response to lapsed time intervals and sensed events. A pacing mode also includes various parameter settings such as the AV delay interval for atrial tracking and/or atrio-ventricular sequential pacing modes. For a given patient, different combinations of pacing configurations and modes may yield differing degrees of therapeutic benefit. Clinical testing of the patient while the device is operating is commonly employed to select a particular pacing configuration and mode that is optimum for that particular patient. A parameter commonly used in optimizing ventricular resynchronization pacing is the maximum rate of systolic pressure rise in the left ventricle, referred to herein as the LV max dP/dt. The LV max dP/dt can be measured with a Swan-Ganz catheter and is commonly used as a surrogate for myocardial contractility. Ventricular resynchronization pacing that increases the LV max dP/dt parameter can be assumed to be effective in restoring coordination of ventricles that has been lessened by conduction defects and in increasing cardiac output.

In accordance with the invention, the controller of a pacemaker such as illustrated in FIG. 1 is programmed to pace the heart with a particular pacing configuration and associated pacing mode, where a pacing configuration is made up of selected pacing channels that the controller uses to output pacing pulses by operating the pulse generator of that channel. The pacemaker controller is also programmed to perform capture verification testing at selected times in order to test a selected sensing/pacing channel for presence or loss of capture during a pacing pulse. As explained above, the capture verification test is performed by sensing whether an evoked response occurs during a capture detection window following the output of a pacing pulse. A loss of capture occurring in a pacing channel can be due, for example, to lead dislodgement or exit block at the electrode. When such a loss of capture occurs in a pacing channel, the selected pacing configuration is compromised and is no longer delivering optimal therapy to the patient. One alternative when this happens is to simply continue pacing with the same pacing mode even though the pacing configuration has been effectively altered by one of the sensing/pacing channels failing to reliably achieve capture. This may not be the most therapeutically beneficial pacing mode for the patient, however, since different pacing configurations may require different pacing modes in order to deliver therapy optimally. In accordance with the invention, the controller is programmed with an ordered list containing different pacing configurations and associated pacing modes. At any point in time, one such pacing configuration and mode is selected for use by the device in delivering pacing therapy to the patient. Upon detection of a loss of capture in a sensing/pacing channel making up the selected pacing configuration, the controller is programmed to switch from the selected pacing configuration and associated pacing mode to a next pacing configuration and associated pacing mode contained in the ordered list. A pacing configuration and mode combination in the list may either be made up of one or more selected sensing/pacing channels and an associated mode that includes one or more parameter settings or may constitute no pacing at all.

The pacing configurations and associated modes in the ordered list may be ranked in order of therapeutic benefit as determined by clinical testing of a particular patient. Such testing may either be performed by measuring the LV max dP/dt parameter or other parameters that have been shown to reflect the hemodynamic effects of resynchronization therapy. The controller may also be programmed to select a next pacing configuration and associated pacing mode from the ordered list that does not employ a sensing/pacing channel in which a loss of capture was detected. For example, if a loss of capture occurs in two or more pacing channels of a multi-site pacemaker, the controller may skip down the list until a pacing configuration is found that does not employ those channels.

The capture verification tests on the pacing channels may be performed using an evoked response sensing channel which may either be a dedicated channel or a channel normally used for other purposes. The test may be performed for each pacing pulse output through a particular channel or at periodic or otherwise selected times. Also, detection of capture loss may constitute one instance of a failure of the capture verification test or may constitute a preset number of such failures. By requiring more than one instances of capture verification failure in a channel before a loss of capture is deemed to have been detected, switching of the pacing configuration is avoided when a spurious loss of capture in a channel occurs that may not happen again.

Figure 3A:
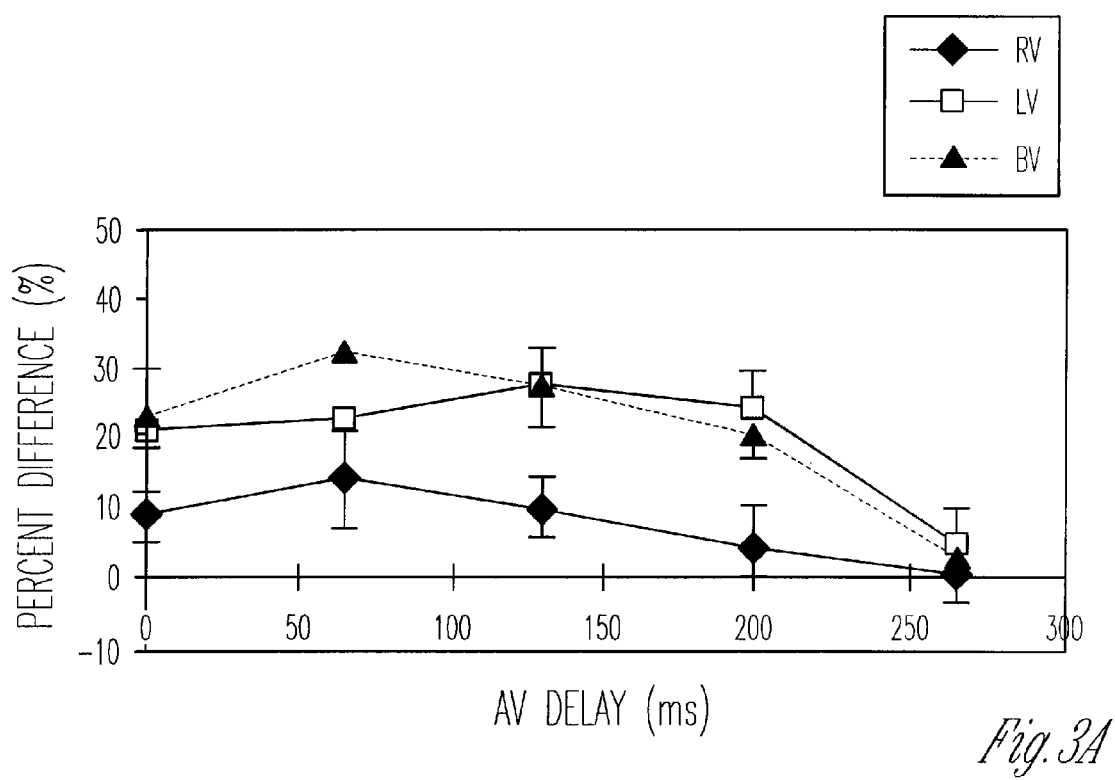
FIGS. 3A and 3B show data obtained from two exemplary patients that illustrate the hemodynamic effects of different AV delay intervals with different pacing configurations.
Figure 3B:
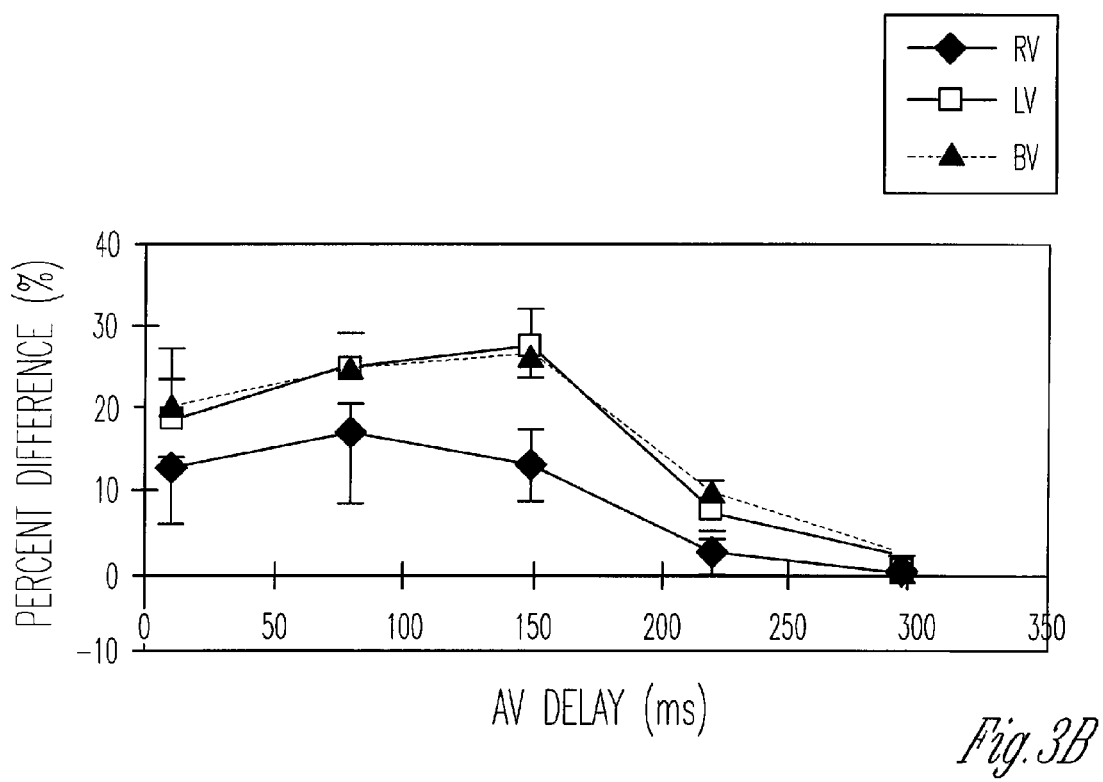

In an exemplary embodiment, a pacemaker is equipped as illustrated in FIG. 1 with two ventricular sensing/pacing channels and one atrial sensing/pacing channel and programmed to deliver ventricular resynchronization therapy with pacing configurations that include both ventricles, the right ventricle only, or the left ventricle only. Each such pacing configuration has an associated atrial tracking and/or sequential atrio-ventricular pacing mode with a particular AV delay interval setting. FIGS. 3A and 3B show data obtained from two example patients during clinical testing of the device using the three pacing configurations with different settings of the AV delay interval. Each data point of the figures represents either a biventricular (BV), left ventricle-only (LV), or right ventricle-only (RV) pacing configuration and shows the percent difference in LV max dP/dt for a given AV delay interval.

FIG. 3A shows that, for this particular patient, the most therapeutically beneficial pacing configuration and mode combination is BV pacing with an AV delay interval of 65 milliseconds. For RV pacing, the optimum AV delay interval is also 65 milliseconds. For the LV pacing configuration, however, the optimum AV interval is 130 milliseconds. An ordered list of the pacing configurations and modes ranked according to therapeutic benefit would then be:

1. BV pacing with an AV delay interval of 65 milliseconds
2. LV pacing with an AV delay interval of 130 milliseconds
3. RV pacing with an AV delay interval of 65 milliseconds The device can thus be initially programmed to operate with BV pacing and an AV delay of 65 milliseconds. If a loss of capture occurs in the left ventricular sensing/pacing channel, the next pacing configuration that does not include that channel is RV pacing also with an AV delay of 65 milliseconds. The device would effectively revert to this even if no pacing configuration and mode switching were to be performed by the device since the left ventricular pacing channel is failing to capture the heart. If a loss of capture occurs in the right ventricular channel, however, the next most therapeutically beneficial pacing configuration and mode combination that does not include the right ventricular channel is LV pacing with an AV delay interval of 130 milliseconds. If no pacing configuration and mode switching in accordance with the invention were performed in this instance, the device would revert to LV pacing but the AV delay interval would still be 65 milliseconds. As shown in FIG. 3A, such a pacing configuration and mode combination would be significantly suboptimal for this particular patient.

FIG. 3B shows data for another example patient and shows that the most therapeutically beneficial pacing configuration and mode combination is either BV pacing with an AV delay interval of 150 milliseconds or LV pacing also with an AV delay interval of 150 milliseconds. For the RV pacing configuration, however, the optimum AV interval is 80 milliseconds. An ordered list of the pacing configurations and modes ranked according to therapeutic benefit would then be:

1. BV or LV pacing with an AV delay interval of 150 milliseconds
2. RV pacing with an AV delay interval of 80 milliseconds If a pacemaker were operating in this patient with BV pacing and an AV delay interval of 150 milliseconds, and a loss of capture were to occur in the LV channel, the device would effectively revert to RV pacing with an AV delay interval of 150 milliseconds if no mode switching is employed. A more therapeutically beneficial result is obtained, however, by switching to the next configuration and mode combination in the list so that the AV delay interval is decreased to 80 milliseconds.

As described above, optimization of the pacing configuration and mode after detection of a loss of capture in a particular channel may be accomplished with an ordered list where various combinations of pacing configurations and mode parameter settings are ranked according to the results of clinical testing. Such ordered lists can be created initially for a particular patient and then updated periodically when follow-up testing is performed. In another embodiment, a cardiac rhythm management device is programmed to optimize one or more pacing mode parameter setting as a result of tests performed by the device itself. For example, a device may incorporate a pressure sensor 500 for detecting left ventricular pressure as shown in FIG. 1. Upon detection of a loss of capture in a particular sensing/pacing channel, the device may then re-optimize the AV delay interval with the residual pacing configuration based upon left-ventricular pressure measurements such as the LV max dP/dt or pulse pressure. Alternatively, if the patient is chronotropically competent, the baroreceptor reflex that controls the atrial rate may be employed to optimize the AV delay interval by selecting the interval that maximizes the atrial cycle length.

Although the invention has been described in conjunction with the foregoing specific embodiments, many alternatives, variations, and modifications will be apparent to those of ordinary skill in the art. Such alternatives, variations, and modifications are intended to fall within the scope of the following appended claims.

What is claimed is:

1. A cardiac rhythm management device, comprising:
a sense amplifier for connecting to an electrode to form an evoked response sensing channel for detecting an evoked response generated after delivery of a pacing pulse;
a plurality of pulse generators for connecting to electrodes to form a plurality of pacing channels for delivering paces to a selected heart chamber;
a controller for controlling the delivery of pacing pulses by a selected pacing configuration in accordance with a programmed pacing mode associated with the pacing configuration, wherein the pacing configuration specifies which pacing channels are to be used for delivery of pacing pulses; and,
wherein the controller is programmed to:
perform a capture verification test at a selected time to test a selected pacing channel for presence or loss of capture during a pacing pulse, the capture verification test being performed by detecting whether an evoked response occurs during a capture detection window following the output of a pacing pulse; and,
switch from the selected pacing configuration and associated pacing mode to a next pacing configuration and associated pacing mode contained in an ordered list upon detection of a loss of capture in a pacing channel making up the selected pacing configuration, wherein the next pacing configuration does not include the pacing channel in which the loss of capture was detected.

2. The device of claim 1 further comprising a switching circuit for switching the input of the evoked response sensing channel to a selected electrode of a pacing channel.

3. The device of claim 1 wherein the pacing configurations and associated modes in the ordered list are ranked in order of therapeutic benefit as determined by clinical testing of a particular patient.

4. The device of claim 1 wherein the list of pacing configurations and associated pacing modes includes at least one configuration selected from a group consisting of a biventricular pacing configuration, a left ventricular-only pacing configuration, a multi-site single chamber pacing configuration, and a right ventricular-only pacing configuration.

5. The device of claim 1 wherein the pacing mode associated with each pacing configuration includes atrial tracking and/or sequential atrio-ventricular pacing and a selected AV delay interval.

6. The device of claim 5 wherein the controller is programmed to re-optimize the AV delay interval when switching to the next pacing configuration in the ordered list.

7. The device of claim 6 wherein the re-optimization of the AV delay interval is performed based upon atrial cycle length.

8. The device of claim 6 wherein the re-optimization of the AV delay interval is performed based upon pressure measurements.

9. The device of claim 8 wherein the controller is programmed to re-optimize the AV delay interval based upon the maximum rate of systolic pressure rise in the left ventricle, referred to as the LV max dP/dt.

10. The device of claim 1 wherein the list of pacing configurations and associated pacing modes includes a configuration and mode in which no pacing is performed.

11. A cardiac rhythm management device, comprising:
a sense amplifier for connecting to an electrode to form an evoked response sensing channel for detecting an evoked response generated after delivery of a pacing pulse;
a plurality of pulse generators for connecting to electrodes to form a plurality of pacing channels for delivering paces to a selected heart chamber;
means controlling the delivery of pacing pulses by a selected pacing configuration in accordance with a programmed pacing mode associated with the pacing configuration, wherein the pacing configuration specifies which pacing channels are to be used for delivery of pacing pulses;
means for performing a capture verification test to test a selected pacing channel for presence or loss of capture during a pacing pulse, the capture verification test being performed by detecting whether an evoked response occurs following the output of a pacing pulse; and,
means for switching from the selected pacing configuration and associated pacing mode to a next pacing configuration and associated pacing mode contained in an ordered list upon detection of a loss of capture in a pacing channel making up the selected pacing configuration, wherein the next pacing configuration does not include the pacing channel in which the loss of capture was detected.

12. The device of claim 11 further comprising means for detecting an evoked response using a selected electrode of a pacing channel.

13. The device of claim 11 wherein the pacing configurations and associated modes in the ordered list are ranked in order of therapeutic benefit as determined by clinical testing of a particular patient.

14. The device of claim 11 wherein the list of pacing configurations and associated pacing modes includes at least one configuration selected from a group consisting of a biventricular pacing configuration, a left ventricular-only pacing configuration, a multi-site single chamber pacing configuration, and a right ventricular-only pacing configuration.

15. The device of claim 11 wherein the pacing mode associated with each pacing configuration includes atrial tracking and/or sequential atrio-ventricular pacing and a selected AV delay interval.

16. The device of claim 15 further comprising means for re-optimizing the AV delay interval when switching to the next pacing configuration in the ordered list.

17. The device of claim 16 wherein the re-optimization of the AV delay interval is performed based upon atrial cycle length.

18. The device of claim 16 wherein the re-optimization of the AV delay interval is performed based upon pressure measurements.

19. The device of claim 18 wherein the re-optimization means is configured to re-optimize the AV delay interval based upon the maximum rate of systolic pressure rise in the left ventricle, referred to as the LV max dP/dt.

20. The device of claim 11 wherein the list of pacing configurations and associated pacing modes includes a configuration and mode in which no pacing is performed.

* * * * *